(12) United States Patent
Bian et al.

(10) Patent No.: US 8,114,611 B2
(45) Date of Patent: Feb. 14, 2012

(54) AFFINITY CHROMATOGRAPHY MATRICES AND METHODS OF MAKING AND USING THE SAME

(75) Inventors: Nanying Bian, Nashua, NH (US); John Charkoudian, Carlisle, MA (US); Neil Soice, Amherst, NH (US); Joaquin Umana, Stoneham, MA (US); Chen Wang, Acton, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

(21) Appl. No.: 12/916,978

(22) Filed: Nov. 1, 2010

(65) Prior Publication Data

US 2011/0105730 A1    May 5, 2011

Related U.S. Application Data

(62) Division of application No. 12/590,726, filed on Nov. 13, 2009, now Pat. No. 7,846,682, which is a division of application No. 11/650,093, filed on Jan. 5, 2007, now Pat. No. 7,833,723.

(60) Provisional application No. 60/756,873, filed on Jan. 6, 2006.

(51) Int. Cl.
*G01N 33/53* (2006.01)
(52) U.S. Cl. .......................... 435/7.1; 435/7.2; 436/518
(58) Field of Classification Search .................. None
See application file for complete search history.

(56) References Cited

U.S. PATENT DOCUMENTS

| | | | |
|---|---|---|---|
| 3,932,557 A | 1/1976 | Matthews | |
| 4,210,723 A | 7/1980 | Dorman | |
| 4,772,635 A | 9/1988 | Mitschker et al. | |
| 5,089,605 A | 2/1992 | Profy et al. | |
| 5,250,613 A | 10/1993 | Bergstrom et al. | |
| 5,260,373 A | 11/1993 | Profy et al. | |
| 5,543,054 A | 8/1996 | Charkoudian et al. | |
| 5,874,165 A | 2/1999 | Drumheller | |
| 6,399,750 B1 | 6/2002 | Johansson | |
| 2004/0171103 A1* | 9/2004 | Bradley et al. | 435/68.1 |
| 2005/0282294 A1 | 12/2005 | Britsch | |
| 2006/0134805 A1 | 6/2006 | Berg et al. | |
| 2009/0275513 A1* | 11/2009 | Rebbeor et al. | 514/12 |

FOREIGN PATENT DOCUMENTS

| | | |
|---|---|---|
| EP | 0266580 | 10/1997 |
| EP | 1352957 | 10/2003 |
| JP | 61-166861 A | 7/1986 |
| WO | 84/03053 A1 | 8/1984 |
| WO | WO2004074471 | 9/2004 |

OTHER PUBLICATIONS

Frost et al, Covalent Immobilization of Proteins to N-Hudroxysuccinimide Ester Derivatives of Agarose, Biochimica et Biophysica Acta. 670 (1981) 163-169.
Boyle Reis, Bacterial Fc Receptors, Biotechnology 5:697, 1987.
Charkouian et al., Membrane Surface For Carbohydrate Analysis, Analytical Letters, 28:1055, 1995.
Porath and Fornstedt, Group Fraction of Plasma Proteins on Dipolar Ion Exchagners, J. Chromatography, 51:479, 1970.
Catimel, B. et al. "Kinetic analyis of the interaction between the monoclonal antibody A33 and its colonic epithelial antigen by the use of an optical biosensor. A comparison of immobilsation strategies." J. Chromatography, 776(1), 15-30, Jul. 25, 1997.
Volke Daniela et al., "Purification of bovine Tau versions by affinity chromatography," Protein Expression and Purification, 501(1), 37-42, Nov. 1, 2006.
International Search Report, International Application No. PCT/US2007/000366. International Application Filing Date Jan. 5, 2007. Search Completion Date Jun. 21, 2007.
Morag et al., analytical biochem 1996, vol. 243, p. 257-263.
International Preliminary Report on Patentability received for PCT Patent Application No. PCT/US2007/000366, issued on Jul. 8, 2008, 5 pages.

* cited by examiner

*Primary Examiner* — Jacob Cheu (57) ABSTRACT

The invention provides methods of coupling protein ligands to a solid support. The invention also provides affinity chromatography matrices and methods of using affinity chromatography matrices to purify a target molecule.

17 Claims, 6 Drawing Sheets

AFFINITY CHROMATOGRAPHY MATRICES AND METHODS OF MAKING AND USING THE SAME

RELATED APPLICATIONS

This application is a divisional patent application of U.S. patent application Ser. No. 12/590,726, filed Nov. 13, 2009, which is a divisional patent application of U.S. patent application Ser. No. 11/650,093, filed Jan. 5, 2007, which claims the benefit of priority of U.S. Provisional Application No. 60/756,873 filed Jan. 6, 2006, each of which are hereby incorporated by reference herein in their entirety.

FIELD OF THE INVENTION

The invention relates generally to the field of chromatography. In certain specific embodiments the invention provides matrices and methods relating to affinity chromatography.

BACKGROUND OF THE INVENTION

Chromatographic methods generally are used to separate and/or purify molecules of interest such as proteins, nucleic acids and polysaccharides from a mixture. Affinity chromatography specifically involves passing the mixture over a matrix having a ligand specific (i.e. a specific binding partner) for the molecule of interest bound to it. Upon contacting the ligand, the molecule of interest is bound to the matrix and thus retained from the mixture. Affinity chromatography provides certain advantages over other types of chromatography. It provides a purification method that is highly specific, fast, economical and high yielding.

In one application affinity chromatography may be used to purify proteins such as monoclonal antibodies. As an example, antibodies of the IgG subtype may be affinity purified by passing them over a matrix having protein A or protein G bound to it (Boyle and Reis, 1987, *Biotechnology* 5:697; Hermanson et al., 1992, *Immobilized Affinity Ligand Techniques*, Academic Press; U.S. Patent Publication No. 2006/0134805).

Methods of attaching protein ligands, such as protein A and protein G to a solid support, e.g., chromatographic media have been previously described, see, e.g., Hermanson et al. 1992, *Immobilized Affinity Ligand Techniques*, Academic Press; U.S. Pat. Nos. 5,874,165; 3,932,557; 4,772,635; 4,210,723; 5,250,6123; European Patent Application EP 1 352 957 A1, WO 2004/074471. Typically, the media is activated with a reactive functional group ("activated group") such as an epoxide (epichlorohydrin), cyanogens (cyanogens bromide (CNBr)), N,N-disuccinimidylcarbonate (DSC), aldehyde or an activated carboxylic acid (e.g. N-hydroxysuccinimide (NHS) esters, carbonyldiimidazole (CDI) activated esters). These activated groups can be attached directly to the base matrix, as is the case for CNBr, or they can be part of a "linker" or spacer molecule which is typically a linear chain of carbon, oxygen and nitrogen atoms, such as the ten membered chain of carbon and oxygen found in the linker butanediol digycidyl ether (a common epoxide coupling agent). The activated media is then equilibrated with the protein ligand under coupling conditions. Once the coupling reaction is finished, the media is washed thoroughly. For Protein A, typically 4-6 mg of protein (ligand density) may be loaded per ml of media resulting in an IgG maximum static capacity (Qs) of 40 g/L. Protein ligand density determines static capacity. The static capacity provides an upper limit of the protein capacity that can be used during the chromatographic separation. In general, the dynamic or loading capacity (Qd) correlates the static capacity with for a given media.

A recombinant form of protein A suitable for attachment to an agarose support has also been described. The recombinant form of the protein is engineered to have a terminal cysteine, see, e.g., U.S. Pat. No. 6,399,750; *GE Healthcare Product Literature for r-Protein A Sepharose Fast Flow, Mabselect® and Mabselect Xtra®*. Using this recombinant Protein A, IgG static capacities ranging from 55-70 g/L have been achieved. However, one limitation associated with using this recombinant protein A ligand is that it must be genetically engineered to contain the selective coupling functionality which may be time consuming and expensive.

Another strategy for coupling of a protein ligand to a solid support is "linker assisted coupling". Linker assisted coupling, in contrast to ligand assisted coupling described in detail below is characterized by its reliance on a single molecule which includes both the ligand (i.e. the specific binding partner of the target molecule to be purified) and a suitable associative functionality which may assist in coupling the ligand to the solid support. This technique involves engineering a functional group (such as a charged amine) into to a linker or spacer designed to couple the protein ligand of interest. The linker in these systems also possesses an activated group for coupling the protein to the linker. The linker is first associated with the solid support and then contacted with protein. Therefore, the single molecule linker serves the dual role of covalently attaching the protein to the matrix and interacting non-covalently with the protein. This provides some pre-association of the entities before/during the coupling reaction. This technique was exploited to couple glycans to a membrane surface for membrane blotting of electrophoresis gels (U.S. Pat. No. 5,543,054; Charkoudian et al., 1995, *Analytical Letters,* 28:1055).

Another example of linker assisted coupling is found in the commercial product Affi-Gel 15® (BioRad, Hercules, Calif.). Affi-Gel 15® is an agarose support derivatized with an NHS activated carboxylic acid as part of a linker arm containing a positively charged functionality. The positively charged functionality is a secondary amine. This amine is protonated at pH 7.4 and allows for coupling of proteins with an isoelectric point (pI) less than 6. The properties of the Affigel matrix, and other such ligands created by linker assisted coupling have limitations because the associative group (positive charge) is part of the protein coupling linker affording a fixed 1:1 ratio of the two functionalities. Another charged linker arm is described for coupling Protein A to agarose in U.S. Pat. No. 5,260,373. Here a shorter linker arm comprised of arginine is used to facilitate protein coupling to an agarose support. The arginine linker is activated with NHS and carries a positive charge. The results suggest, however, that only a modest improvement in IgG binding capacity is attained compared to non-linker assisted coupling. Moreover, the 1:1 ratio described above is maintained here as well. Protein A bound to a solid support via a linker has recently been described in U.S. patent application Ser. No. 10/928,731.

Scale up of fermentation and tissue culture methods, e.g., for the production of monoclonal antibodies, has resulted in both increased volumes and increased concentrations of target molecules produced by these methods. Product concentrations exceeding 1 gram per liter are not uncommon. These products require purification before they may be marketed. Accordingly, a need exists for a chromatographic matrix having enhanced binding capacity that provides good product yield, and which is economical and easy to manufacture. Various embodiments of the invention described below meet these and other needs.

SUMMARY OF THE INVENTION

In certain embodiments, the invention provides a method of making an affinity chromatography matrix wherein the matrix comprises a solid support and at least one protein ligand and wherein the method comprises a) contacting the solid support with an associative group such that the associative group reacts with the solid support; b) activating the solid support (i.e. addition of an activated group); c) contacting the solid support with the protein ligand such that the protein ligand binds to the solid support and interacts with the associative group of a).

In certain other embodiments the invention provides an affinity chromatography matrix comprising: a) a solid support; b) a protein ligand bound to the solid support; and c) an associative group separately bound to the solid support where the associative group interacts with the protein ligand.

In still other embodiments the invention provides a method of purifying a target molecule from a mixture comprising 1) contacting the mixture under a first set of conditions with an affinity chromatography matrix such that the target molecule binds to the protein ligand of the matrix where the affinity chromatography matrix comprises a) a solid support; b) a protein ligand bound to the solid support; and c) an associative group separately bound to the solid support where the associative group interacts with the protein ligand; and 2) altering the conditions of 1) such that the target molecule no longer binds to the protein ligand of the matrix, thereby purifying the substance of interest. Optionally, one or more wash steps employing a suitable wash reagent, e.g., phosphate-buffered saline, water, or a supplemented buffer described infra, may be performed between steps 1 and 2. The matrix may also be equilibrated with an appropriate buffer prior to step 1.

In yet other embodiments the invention provides a method of coupling a protein ligand to a solid support comprising a) contacting the solid support with a associative group such that the associative group reacts with the solid support; b) activating the solid support; c) contacting the solid support with the protein ligand such that the protein ligand binds to the solid support and interacts with the associative group of a).

In certain further embodiments the invention provides a method of coupling protein A to an agarose support comprising a) contacting the agarose support with a charged species such that the charged species reacts covalently with the agarose support; b) activating the agarose support with an activating group; c) contacting the agarose support with the protein A such that the protein A covalently binds to the solid support and non-covalently interacts with the charged species of a).

In still other embodiments the invention provides an affinity chromatography matrix comprising: a) an agarose support; b) protein A covalently bound to the agarose support; and c) a charged species, which covalently binds with the solid support and non-covalently interacts with the protein A.

In yet other embodiments the invention provides an agarose bead comprising at least 10 g/L of protein ligand bound to the surface of the agarose bead. The protein ligand may serve as an affinity ligand, e.g. Protein A, Protein G, and thus be a specific binding partner of a target molecule, e.g., protein of interest.

In some embodiments the protein ligand binds, e.g., covalently, to the solid support via an activated functional group without any intervening linker molecule. The protein ligand may also non-covalently interact with one or more associative groups, which are covalently bound via a distinct covalent bond to the solid support with or without any intervening linker molecules. Thus in certain embodiments the invention provides an associative group coupled to a solid support which is non-linker assisted. In certain embodiments the invention provides a protein ligand coupled to a solid support which is non-linker assisted. In certain embodiments the associative group and the protein ligand are each separately coupled via a covalent bond to the solid support.

In other embodiments the protein ligand binds, e.g., covalently, to the solid support via an activated functional group with an intervening linker molecule. The protein ligand may also non-covalently interact with one or more associative groups, which are covalently bound to the solid support without any intervening linker molecules. Thus in certain embodiments the invention provides an associative group coupled to a solid support which is non-linker assisted and a protein ligand coupled to a solid support which is linker assisted.

In other embodiments the invention provides an associative group coupled to a solid support and a protein ligand coupled to a solid support where some partial population of the associative group and the protein ligand is coupled to the solid support via a linker. Some population of protein ligand may be coupled to the solid support via a linker or some population of the associative group may be coupled to the solid support via a linker. In some embodiments both the associative group and the protein ligand will have populations which are coupled to the solid support via different linkers.

In still other embodiments the invention provides a linker assisted associative group coupled to a solid support, e.g., by a covalent bond. The associative group may interact, e.g., non-covalently, with a protein ligand covalently coupled to a solid support without any intervening linker molecule.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DESCRIPTION OF THE EMBODIMENTS

Methods of Coupling Ligands to a Solid Support

In certain embodiments the invention provides methods of coupling a protein ligand (e.g. ligand assisted coupling), to a preformed solid support, such as chromatographic media, wherein both the activating agent, which covalently binds the protein ligand, and the associative group, which interacts non-covalently with the protein ligand and thus facilitates the formation of the covalent bond between the protein ligand and the activating agent, are both linked to the solid support by a separate and distinct reaction and wherein the activating agent and the associative group are not linked prior to the reactions covalently linking them to the solid support. The method may comprise a) reacting an associative group with a solid support b) activating the solid support and c) coupling a protein ligand to the solid support. In certain embodiments both the associative group and the protein ligand may be covalently linked to the solid support, but are not covalently linked to each other, except through the solid support. Both the associative group and the activating agent may be covalently bound to the outer surface of the solid support. The protein ligand may be covalently bound to the activating agent, which is bound to the solid support. The associative group may interact with the protein ligand, e.g. non-covalently, thus facilitating the formation of the covalent bond between the protein ligand and the activating agent which is covalently bound to the outer surface of the solid support. It is also contemplated that both the protein ligand and the associative group may bind accessible interior surfaces and pores of a solid support.

It will be appreciated that steps a) and b) may be performed in any order. Thus in some embodiments the invention provides a two step reaction which may be used to couple an associative group and protein ligand to a solid support. Independently performing steps a)-c) provides a number of advantages, including flexibility in the choice of associative groups, protein ligands and solid supports, and control over the ratio of associative group to protein ligand to enable optimization of conditions for performing the desired affinity chromatography. This contrasts with previously described methods of coupling protein ligands to solid supports, e.g. linker assisted coupling, which necessarily results in a 1:1 ratio of protein ligand and associative group.

In previously described methods the activating agent and the associative group are either covalently linked to each other before being bound to the solid support or are incorporated directly into a solid support as part of the polymerization reaction forming the solid support. These methods offer little flexibility and less than optimal control over ligand density. Other previously described methods such as random coupling or multiple point attachment rely on any amine groups available in a protein ligand. Multiple point attachment offers little flexibility or control over protein ligand coupling to a solid support.

Additional advantages according to the invention include the use of two or more different associative groups and/or the use of two or more different protein ligands. Yet other advantages include the ability to tightly control ligand density to optimize dynamic capacity, static capacity or both. Still other advantages provide limiting the amount of non-specific binding of unwanted contaminants on the matrix. Non-specific binding is a particular problem for previously described methods which rely on coating the solid support with a species, such as an amine containing species, capable of binding a desirable protein ligand. The control of ligand density provided by the invention avoids the high level of non-specific binding found in these previously described methods.

Thus by uncoupling the reactions for binding of the associative group and the activating agent to the solid support, the instant invention provides for better control of the concentration ratios of both the activating agent and the associative group, thereby providing better control and tailoring of the chromatographic conditions, e.g., pH, salt concentration in the buffer, for isolating the target protein. Thus, in certain embodiments the invention contemplates a variety of ratios of protein ligand and associative groups, including ratios where the protein ligand concentration exceeds the associative group and ratios where the concentration of the associative group exceeds the concentration of the protein ligand. It is contemplated that a plurality of different associative groups may be used in various embodiments of the invention. It is also contemplated that a plurality of different activating agents may be used to activate the solid support in various embodiments of the invention. Similarly, it is contemplated that a plurality of different protein ligands may be used in various embodiments of the invention.

Protein ligand, as used herein, refers to a protein that is bound to a solid support and which is suitable for specifically binding a target molecule of interest. A protein may include a full length protein, a fragment or subunit of the full length protein, a polypeptide, or peptide fragment of a protein.

In some embodiments the methods of the invention provide for coupling high density protein ligands to a solid support. This in turn may enhance the binding capacity, e.g., static capacity ($Q_s$) and dynamic capacity ($Q_d$), of the target molecule as compared to previously described methods. As an example, using previously described methods typically 4-6 mg of n-protein A (i.e., protein A derived from *Staphylococcus* A) per ml of solid support may be loaded. Using the methods of the invention 7-100 mg of protein A per ml of solid support may be loaded. In certain embodiments more than 10 mg/ml of protein A may be loaded on a solid support. In other embodiments at least 8 mg/ml may be loaded on a solid support. In some embodiments of the invention enhanced static and dynamic capacities are attained without either recombinantly altering the protein A, e.g. by the addition of a cysteine residue, or by relying on linker assisted coupling.

In certain embodiments the method of the invention comprises contacting the solid support with at least one associative group that is capable of reacting with the solid support. The solid support may be already formed, e.g. a polymerized support, which may be reacted with at least one associative group. In other embodiments the solid support may not be preformed, e.g. non-polymerized, such that the associative group is added to chemical constituents that are subsequently reacted to form a solid support with an incorporated associative group. The reaction between the solid support and the associative group may result in the formation of a covalent bond between the solid support and the associative group. The associative group may thus be covalently bound to the outer surface of the solid support and may also be bound to accessible interior surfaces, e.g. pores.

Non-covalent interactions involving the associative group, such as ionic interactions, hydrophobic interactions, van der Waals forces and hydrogen bonds are also contemplated. As an example, the associative group may interact non-covalently with a charged molecule, e.g., a polymer that is covalently attached to the solid support. The associative group may also interact with the protein ligand. Thus, the solid support may be activated such that the protein ligand covalently binds to the solid support and non-covalently interacts with the associative group. The non-covalent interaction may thus facilitate the covalent binding of the protein ligand to the solid support.

In some embodiments the associative group may directly react with the solid support without the need for any intervening or linking molecules. In other embodiments the associative group may be provided as a mixture where a first population of the associative group reacts with the solid support directly, and a second population of the associative group reacts with the solid support indirectly through one or more linker molecules. In addition, the associative group may be modified by activation with a linker molecule thereby incorporating at least some of the associative group into the linker molecule while also permitting some of the associative group to react directly, e.g., covalently bind, the solid support. Due to the nature of certain chemical reactions, the associative group designed to interact non-covalently with the protein ligand may react with the activating group, thus eventually coupling the protein ligand to the solid support through a linker arm containing both the associative group and the activating group. However, these activation reactions modify both the solid support and the associative group, creating a distribution of protein coupling sites. One population of these sites comprises an activated group linked to the solid support through the associative group (as would be the case with a CNBr activated secondary amine). A second population may exist, where the coupling sites are comprised of an activated group directly attached to the base matrix and unmodified associative groups (as would be the case with a CNBr activated base matrix with residual unmodified secondary amines). This is one example of differences between "linker assisted coupling" (where only one population of coupling sites may exists) and "ligand assisted coupling" (where at least two variable populations of coupling sites may exist). A wider range of coupling conditions and configurations can be utilized, because the associative group and the activating group can be independently varied in the type, amount and reactivity of the groups involved.

All non-covalent interactions between the associative group and the protein ligand are contemplated. The non-covalent interaction with the protein ligand may include, for example, an ionic interaction, a hydrophobic interaction, an interaction mediated by hydrogen bonding or van-der Waals forces.

In one embodiment the interaction between the associative group and the protein ligand may be ionic. As an example a positively charged associative group can be bound to the solid support. The solid support may then be activated with a chemical functionality that will facilitate chemical binding, e.g., covalent binding, of the protein ligand to the solid support. The pH of the solution containing the protein ligand may be adjusted such that the protein carries a charge complementary to the charge of the associative group associated with the solid support, e.g., at least one negative charge or a net negative charge. The interaction between the positively charged associative group bound to the solid support and the negatively charged protein will facilitate the bonding of the protein ligand to the activated solid support and thus provide enhanced binding capacity compared to previously described methods. The charged species may be an ion, or a molecule with a net charge.

Choosing the appropriate buffer conditions for coupling a protein ligand to a solid support is well within the capability of the skilled artisan. Suitable buffers include any non-amine containing buffer such as carbonate, bicarbonate, phosphate and acetate buffers. Salt concentration of the buffer will depend on the associative group used. As an example the salt concentration may be in the range of 5 nM-100 mM. Where a charged species is used the salt concentration may be at least 5 nM but less than 0.1M, at least 5 nM but less than 0.01M, at least 5 nM but less than 0.001M. In certain embodiments the salt concentration may be 0.01M. Where a hydrophobic species is used a high salt concentration may be desirable. Thus the salt concentration may be greater than 0.001 M, greater than 0.01 M, greater than 0.1 M.

The method of the invention may be performed at a temperature ranging from 0° C. to 99° C. In certain embodiments the method may be practiced at a temperature less than 60° C., less than 40° C. less than 20° C., less than 10° C. In some embodiments the method of the invention may be practiced at a temperature of 4° C. In other embodiments the method of the invention may be practiced at a temperature of 20° C.

Associative Groups

Associative groups suitable for use in the invention include charged species such as ionic species, and uncharged species such as hydrophobic species. The associative group may modify the solid support, e.g. by covalently binding directly with the solid support. Suitable examples of ionic species may include quaternary amines, tertiary amines, secondary amines, primary amines, sulfonic acid, carboxylic acid, or any combination thereof. Suitable examples of hydrophobic species may include a phenyl group, a butyl group, a propyl group, or any combination thereof. It is also contemplated that mixed mode species may be used, e.g. a mixture of charged and hydrophobic species. The associative group may also interact with the protein ligand. Thus the interaction between the associative group and the protein ligand may be comprised of a mixture of interactions, e.g. ionic and hydrophobic species.

The associative group may be covalently coupled to the solid support by reacting a functional group on the solid support with a functional group on the associative group. Suitable functional groups include, but are not limited to amines, hydroxyl, sulfhydryl, carboxyl, imine, aldehyde, ketone, alkene, alkyne, azo, nitrile, epoxide, cyanogens and activated carboxylic acid groups. As an example agarose beads contain hydroxyl groups which may be reacted with the epoxide functionality of a positively charged associative group, such as glycidyl trimethylammonium chloride. A skilled artisan will appreciate that a plurality of associative groups may be coupled to the solid support provided that at least one bifunctional associative group is used. Thus associative groups may be coupled in tandem to the solid support or they may be individually coupled directly to the solid support.

Protein Ligands and Target Molecules

Any protein ligand may be used in the practice of the invention provided that it is a specific binding partner of a target molecule of interest. Examples of protein ligands may include Protein A, Protein G, the Fc receptor of an antibody, a receptor for a hormone or growth factor. The protein ligand may be an immunoglobulin, e.g. IgG, IgM, IgA, IgD, IgE or a fragment thereof. Fragments may include immunoglobulin fragments which retain the ability to bind the target antigen epitope, and/or bind to an Fc receptor and/or Protein A and/or Protein G. The protein ligand may be an Fc molecule or fragment thereof; a Fab or the like; an enzyme, e.g. glutathione transferase, a tyrosine kinase, e.g. MAP, Src, Lck; a substrate, e.g. glutathione. The protein ligand may be a protein tag such as a polypeptide comprising one or more histidines. The protein ligand may be a fusion protein such as Embrel®. The protein ligand may be a nucleic acid binding protein such as a transcription factor, reverse transcriptase, topo-isomerase, helicase. If the target molecule is a receptor, its ligand, e.g., the growth factor, may serve as the protein ligand in the methods of this invention. Where the target molecule is an immunoglobulin, e.g., IgG or a fragment thereof containing at least a portion of an Fc region, the protein ligand may be Protein A, Protein G or a functional fragment thereof. A functional fragment thereof may include a Protein A fragment or a Protein G fragment that retains the capability of binding to an Fc region, or Fc fragment, of an IgG.

The protein ligand may be a naturally occurring molecule or an engineered molecule. In certain embodiments it may be desirable to genetically alter naturally occurring protein ligands to facilitate either binding to a solid support or orientation of the protein ligand on the solid support or both. Thus, depending on the associative group used, the skilled artisan may engineer charged groups or hydrophobic groups, or both, into the protein ligand. These changes may be made anywhere within the protein ligand.

Where the protein ligand is protein A, the invention provides for a static binding capacity Qs of greater than 50 mg/ml if n-protein A (naturally occurring) is used and greater than 65 mg/ml if r-protein A (recombinant protein A) is used. The recombinant protein A may include modifications other than a terminal cysteine.

Where the solid support is provided in solution, e.g. a bead, a suitable concentration of protein ligand may range from 0.05-700 µmols/ml of solid support, 0.1-100 µmols/ml of solid support.

Target molecules may include any molecule which specifically binds to the protein ligand of choice. Where the protein ligand is protein A or protein G the target molecule may include an immunoglobulin of the IgG subclass. A specific example of a target molecule would include a monoclonal antibody. Fragments of immunoglobulins are also contemplated provided that they retain their ability to bind to the protein ligand of choice. The target molecule may also be a fusion protein including an Fc fusion protein such as Embrel®.

Solid Supports and Activating Agents

Any porous material may be used as a solid support. As an example, but not as a limitation, the porous material may take the form of a membrane, a bead, a gel, a cassette, a column, a chip, a slide, a plate or a monolith.

The porous material may be comprised of an organic or inorganic molecules or a combination of organic and inorganic molecules and may be comprised of one or more functional groups, e.g., an hydroxyl group, suitable for reacting, e.g., forming covalent bonds with either the associative group, the activating agent or both. The porous material may be comprised of a hydrophilic compound, a hydrophobic compound, an oleophobic compound, an oleophilic compound or any combination thereof. The porous material may be comprised of a polymer or a copolymer.

Examples of suitable porous materials, include, but are not limited to polyether sulfone, polyamide, e.g., agarose, cellulose, a polysaccharide, polytetrafluoroethylene, polysulfone, polyester, polyvinylidene fluoride, polypropylene, a fluorocarbon, e.g. poly (tetrafluoroethylene-co-perfluoro(alkyl vinyl ether)), poly carbonate, polyethylene, glass, polycarbonate, polyacrylate, polyacrylamide, poly(azolactone), polystyrene, ceramic, nylon and metal.

The solid support may be activated with an appropriate chemical functionality. Suitable chemical functionalities may include cyanogens, e.g. cyanogen bromide, aldehyde, epoxide, and activated carboxylic acid, e.g. N-hydroxysuccinimide esters or any combination thereof. Alternatively, where the associative group is a primary, a secondary, or tertiary amine, the associative group may be activated with epichlorhydrin or a difunctional epoxide.

Linkers

In some embodiments the invention provides associative groups and/or protein ligands which may be coupled to a solid support via an intervening linker. The linker may comprise at least one functional group coupled to a linking moiety. The linking moiety may comprise any molecule capable of being coupled to a functional group. Thus the linking moiety may include any alkyl, alkenyl, or alkynyl group. The linking moiety may comprise a carbon chain ranging from 1 to 30 carbon atoms. In some embodiments the linker may be comprised of more than 30 carbon atoms. The linking moiety may comprise at least one hetero-atom such as nitrogen, oxygen and sulfur. The linking moiety may be comprised of a branched chain, an unbranched chain or a cyclic chain. The linking moiety may be substituted with two or more functional groups. In one specific embodiment the linker may comprise of the following attached through a hydroxyl group to agarose: $CH_2CH_2N(CH_2CH_3)_2CH_2CH(OH)CH_2O(CH_2)_4$ $OCH_2CH(O)CH_2$.

Methods of Purifying a Target Molecule

In certain embodiments the invention provides a method of purifying a target molecule from a mixture. The target molecule may be any molecule with a specific binding partner provided that the specific binding partner may be coupled to a solid support. Examples of target molecules may include proteins such as immunoglobulins. The immunoglobulins may be polyclonal antibodies or a monoclonal antibody or a functional fragment thereof. Functional fragments may include any fragment of an immunoglobulin comprising a variable region that still binds specifically to its antigen while at the same time retaining its ability to specifically bind to a protein ligand coupled to a solid support.

In certain embodiments the method comprises a) contacting a solid support of the invention (as described herein) with a mixture comprising a target molecule under a first set of conditions such that the target molecule specifically binds to the protein ligand, coupled to the solid support and b) altering the conditions such that the target molecule no longer binds to the affinity ligand. In certain embodiments the method comprises altering the pH between step a) and step b). In some embodiments step b) may be performed at a pH that is more acidic than the pH of step a). In certain embodiments step b) comprises altering the pH. Thus step a) may be performed at a neutral pH, or a pH ranging from 6-8 and step b) may be performed at an acidic pH, e.g., a pH ranging from 1-6. In other embodiments the method comprises altering the salt concentration of the buffer. Thus in one embodiment a high salt concentration, e.g., >0.1 M, may be used in step a) and/or a low salt concentration, e.g., <0.1M may be used in step b). In other embodiments a low salt concentration, <0.1M may be used in step a) and/or a high salt concentration may be used in step b). In still other embodiments the pH and/or the salt concentration of the buffer may be altered between step a) and step b).

1. Intermediate Washing of Chromatographic Matrices

In certain embodiments the invention also provides a method of washing a chromatography matrix to remove non-specifically bound contaminants and thus obtain a purer final product. The matrix may include any chromatographic matrix known in the art. As an example, the chromatography matrix may be an affinity matrix. The affinity matrix may be any of the affinity matrices described herein, including an affinity matrix which is made by ligand assisted coupling. The method may include an intermediate wash which is performed after the target molecule has bound to the chromatographic matrix. Typically non-specific adsorbed contaminants may include any components except the target molecule or product. Examples of non-specifically bound contaminants may include proteins, DNA, lipids, endotoxins, viral particles, and other small molecules including phenol red, peptone, pluronic F68, an amino acid.

The intermediate washing reagent may comprise an equilibrating buffer or a buffer having similar pH and salt concentrations as the feed (i.e. the solution containing the unpurified sample), and further comprising a) an elevated concentration of salts (e.g, sodium chloride, ammonium chloride, sodium sulfate, potassium chloride, ammonium sulfate, etc), or b) a different pH (lower or higher), or c) combinations of a) and b), or d) additives, e.g., surfactants (e.g., Tween), amino acids and derivatives thereof, or an organic solute (e.g., ethylene glycol). The intermediate wash may reduce non-specific binding of certain species by 2-5 fold when compared with wash solutions such as PBS. In some embodiments more than a five fold reduction of non-specific binding of certain species is achieved when compared to known wash solutions such as PBS.

In certain embodiments the invention provides a method of washing an affinity matrix to remove non-specifically bound species comprising contacting an affinity matrix with a buffer having a slightly basic pH (e.g. 7.3-7.5) and a supplemented salt concentration ranging from 0-1M. Thus the buffer may be PBS, or any other suitable buffer, that is further supplemented with additional salt. In some embodiments the salt concentration ranges from 0.15M to 1M. In yet other embodiments the salt concentration ranges from 0.25M to 1M. In still other embodiments the salt concentration ranges from 0.25M to 0.5M. In some embodiments the salt concentration is greater than 0.0001M, but less than 0.8M.

In other embodiments the buffer, e.g. PBS or any other suitable buffer, may have an acidic pH (e.g., 6.5) and a supplemented salt concentration that is less than 1M, but greater than 0.0001M (e.g., 0.4M). In still other embodiments the buffer may have a slightly basic pH (e.g. 7.3-7.5). In some embodiments the wash buffer may comprise one or more charged amino acids. The wash buffer may comprise an amino acid or an alkylated amino acid including betaine, L-alanine, glycine, valine, glutamic acid, and lysine. The amino acid or alkylated amino acid may be present at a concentration ranging from 0.25M to 0.5M. In certain embodiments the concentration of the amino acid or alkylated amino acid is less than 0.5M, but greater than 0.0001M. In still other embodiments the concentration of the amino acid or alkylated amino acid may range from 0.0001M to 1M.

Suitable amino acids which may be used in an intermediate wash buffer include, but are not limited to glycine, valine, lysine, arginine, aspartic acid, glutamic acid, as well as amino acid derivatives such as n-methyl glycine, and trimethyl β-alanine. In some embodiments where the intermediate wash buffer comprises a buffer supplemented with an amino acid or an amino acid derivative, the buffer may have a slightly acidic pH, e.g. in the range of 6.0-6.99.

EXAMPLES

Example 1

Ligand Assisted Coupling Using Quaternary Amine Ligands, Cyanogen Bromide and n-Protein A (14/mg/ml)

Agarose beads (Sepharose 4B) (GE Healthcare, Piscataway N.J.) were crosslinked using epichlorohydrin according to a previously described method (Porath and Fornstedt, 1970, *J. Chromatography*, 51:479). The agarose beads were reacted with positively charged associative group, e.g., cations, according to the following method: 100 mL of beads were added to 100 mL of 75% wt glycidyl trimethylammonium chloride (GTMAC) and 3.3 g 50% wt sodium hydroxide. The reaction was shaken vigorously (>100 rpm) on a rotary shaker overnight at room temperature. The beads were then filtered and washed with three 200 mL volumes of Milli-Q water (Millipore Corp, Billerica, Mass.).

The beads (10 mL) were filtered and then equilibrated in 20 mL 1M $Na_2CO_3$. The sample was chilled on ice along with a second jar containing a solution of 0.5 g CNBr/mL acetonitrile. Once the solutions were chilled, 1.5 mL of the CNBr acetonitrile solution was added to the beads and the beads were placed on a shaker (>100 rpm) on ice. Two minutes later another 1.5 mL of the CNBr acetonitrile solution was added to the beads and the beads were again placed on a shaker (>100 rpm) on ice. The beads were allowed to react for 4 minutes and then washed with 200 mL ice cold water and 200 mL of ice cold 0.012 M $NaHCO_3$ and filtered. The filtered bead cake (10 mL) was added to 10 mL of 0.012 M $NaHCO_3$ containing 140 mgs of n-Protein A (14 mg/mL). The beads were shaken at room temperature overnight. The beads were then washed with 0.2 M $NaHCO_3$ and filtered. The bead cake was added to 20 mL of 0.5 M ethanolamine in 0.2 M $NaHCO_3$. After 30 minutes the beads were washed with 0.2 M $NaHCO_3$, 0.1 M sodium acetate with 0.5 M NaCl (pH 4.5) and then finally with phosphate buffered saline. Static and dynamic capacity was determined as described below in Example 12.

Example 2

Ligand Assisted Coupling Using Quaternary Amine Ligands, Cyanogen Bromide and n-Protein A (17.8 mg/ml).

Agarose beads (Sepharose 4B) (GE Healthcare, Piscataway N.J.) were crosslinked using epichlorohydrin according to a previously described method (Porath and Fornstedt, 1970, *J. Chromatography*, 51:479). The agarose beads were reacted with positively charged associative groups, e.g., cations, according to the following method: 100 mL of beads were added to 100 mL of 75% wt glycidyl trimethylammonium chloride (GTMAC) and 3.3 g 50% wt sodium hydroxide. The reaction was shaken vigorously (>100 rpm) on a rotary shaker overnight at room temperature. The beads were then filtered and washed with three 200 mL volumes of Milli-0 water (Millipore Corp, Billerica, Mass.).

The beads (10 mL) were filtered and then equilibrated in 20 mL 1M Na2CO3. The sample was chilled on ice along with a second jar containing a solution of 0.5 g CNBr/mL acetonitrile. After the solutions were chilled, 1.5 mL of the CNBr acetonitrile solution was added to the beads and the beads placed on a shaker (>100 rpm) on ice. Two minutes later another 1.5 mL of the CNBr acetonitrile solution was added to the beads and the beads placed on a shaker (>100 rpm) on ice. The beads were allowed to react 4 minutes and then washed with 200 mL of ice cold water and 200 mL of ice cold 0.012 M NaHCO3 and filtered. The filtered bead cake (10 mL) was added to 16 mL of 0.012 M $NaHCO_3$ containing 285 mgs of n-Protein A (17.8 mg/mL). The beads were shaken at room temperature overnight. The beads were then washed with 0.2 M $NaHCO_3$ and filtered. The bead cake was added to 20 mL of 0.5 M ethanolamine in 0.2 M $NaHCO_3$. After 30 minutes the beads were washed with 0.2 M $NaHCO_3$, 0.1 M sodium acetate with 0.5 M NaCl (pH 4.5) and finally phosphate buffered saline. Static and dynamic capacity was determined as described below in Example 12.

Example 3

Ligand Assisted Coupling Using Quaternary Amine Ligands, Cyanogen Bromide and r-Protein A Agarose beads (Sepharose 4B) (GE Healthcare, Piscataway N.J.) were crosslinked using epichlorohydrin according to a previously described method (Porath and Fornstedt, 1970, *J. Chromatography,* 51:479). The agarose beads were reacted with positively charged associative groups, e.g., cations, according to the following method: 100 mL of beads were added to 100 mL of 75% wt glycidyl trimethylammonium chloride (GTMAC) and 3.3 g 50% wt sodium hydroxide. The reaction was shaken vigorously (>100 rpm) on a rotary shaker overnight at room temperature. The beads were then filtered and washed with three 200 mL volumes of Milli-Q water.

The beads (10 mL) were filtered and then equilibrated in 20 mL 1 M $Na_2CO_3$. The sampled was chilled on ice along with a second jar containing a solution of 0.5 g CNBr/mL acetonitrile. After the solutions were chilled, 1.5 mL of the CNBr acetonitrile solution was added to the beads and the beads placed on a shaker (>100 rpm) on ice. Two minutes later another 1.5 mL of the CNBr acetonitrile solution was added to the beads and the beads placed on a shaker (>100 rpm) on ice. The beads were allowed to react 4 minutes and then washed with 200 mL of ice cold water and 200 mL of ice cold 0.012 M $NaHCO_3$ and filtered. The filtered bead cake (10 mL) was added to 10 mL of 0.012 M $NaHCO_3$ containing 250 mgs of commercially available r-Protein A (25 mg/mL). The beads were shaken at room temperature overnight. The beads were then washed with 0.2 M $NaHCO_3$ and filtered. The bead cake was added to 20 mL of 0.5 M ethanolamine in 0.2 M $NaHCO_3$. After 30 minutes the beads were washed with 0.2 M $NaHCO_3$, 0.1M sodium acetate with 0.5 M NaCl (pH 4.5) and finally phosphate buffered saline. Static and dynamic capacity was determined as described below in Example 12.

Example 4

Non-Ligand Assisted Coupling without Quaternary Amine Ligands, Using cyanogen bromide and n-Protein A (17.8 mg/ml)

Agarose beads (Sepharose 4B) (GE Healthcare, Piscataway N.J.) were crosslinked using epichlorohydrin according to a previously described method (Porath and Fornstedt, 1970, *J. Chromatography,* 51:479). The beads were then filtered and washed with three 200 mL volumes of Milli-Q water (Millipore Corp, Billerica, Mass.).

The beads (10 mL) were filtered and then equilibrated in 20 mL 1M $Na_2CO_3$. The sample was chilled on ice along with a second jar containing a solution of 0.5 g CNBr/mL acetonitrile. After the solutions were chilled, 1.5 mL of the CNBr acetonitrile solution was added to the beads and the beads placed on a shaker (>100 rpm) on ice. Two minutes later another 1.5 mL of the CNBr acetonitrile solution was added to the beads and the beads placed on a shaker (>100 rpm) on ice. The beads were allowed to react 4 minutes and then washed with 200 mL of ice cold water and 200 mL of ice cold 0.012 M $NaHCO_3$ and filtered. The filtered bead cake (10 mL) was added to 16 mL of 0.012 M $NaHCO_3$ containing 285 mgs of n-Protein A (17.8 mg/mL). The beads were shaken at room temperature overnight. The beads were then washed with 0.2 M $NaHCO_3$ and filtered. The bead cake was added to 20 mL of 0.5 M ethanolamine in 0.2 M $NaHCO_3$. After 30 minutes the beads were washed with 0.2 M $NaHCO_3$, 0.1 M sodium acetate with 0.5 M NaCl (pH 4.5) and finally phosphate buffered saline. Dynamic and static capacity was determined as described below in Example 12.

Example 5

Non-Ligand Assisted Coupling without Quaternary Amine Ligands, Using Cyanogens Bromide and r-Protein A Agarose beads (Sepharose 4B) (GE Healthcare, Piscataway N.J.) were crosslinked using epichlorohydrin according to a previously described method (Porath and Fornstedt, 1970, *J. Chromatography,* 51:479). The beads were then filtered and washed with three 200 mL volumes of Milli-Q® water (Millipore Corporation, Billerica, Mass.). The beads (10 mL) were filtered and then equilibrated in 20 mL 1M $Na_2CO_3$. The sampled was chilled on ice along with a second jar containing a solution of 0.5 g CNBr/mL acetonitrile. After the solutions were chilled, 1.5 mL of the CNBr acetonitrile solution was added to the beads and the beads placed on a shaker (>100 rpm) on ice. Two minutes later another 1.5 mL of the CNBr acetonitrile solution was added to the beads and the beads placed on a shaker (>100 rpm) on ice. The beads were allowed to react 4 minutes and then washed with 200 mL of ice cold water and 200 mL of ice cold 0.012 M $NaHCO_3$ and filtered. The filtered bead cake (10 mL) was added to 10 mL of 0.012 M $NaHCO_3$ containing 250 mgs of commercially available r-Protein A (25 mg/mL). The beads were shaken at room temperature overnight. The beads were then washed with 0.2 M $NaHCO_3$ and filtered. The bead cake was added to 20 mL of 0.5 M ethanolamine in 0.2 M $NaHCO_3$. After 30 minutes the beads were washed with 0.2 M $NaHCO_3$, 0.1 M sodium acetate with 0.5 M NaCl (pH 4.5) and finally phosphate buffered saline. Dynamic and static capacity was determined as described below in Example 12.

Example 6

Ligand Assisted Coupling Using Quaternary Amine Ligands, Butanediol Diglycidylether and n-Protein A Agarose beads (Sepharose 4B) (GE Healthcare, Piscataway N.J.) were crosslinked using epichlorohydrin according to a previously described method (Porath and Fornstedt, 1970, *J. Chromatography,* 51:479). The agarose beads were reacted with positively charged associative groups, e.g., cations, according to the following method: 50 mL of beads were added to 40 g of 75% wt glycidyl trimethylammonium chloride (GTMAC), 10 mL Milli-Q water and 1.67 g 50% wt sodium hydroxide. The reaction was shaken vigorously (>100 rpm) on a rotary shaker overnight at room temperature. The beads were then filtered and washed with three 100 mL volumes of Milli-Q® water (Millipore Corp, Billerica, Mass.). A sample of the beads was titrated using the protocol described below to determine the quarternary ammonium ligand density.

The beads (50 mL, filtered cake) were added to a jar containing 15 mLs of 4.6M NaOH. The mixture was slurried and then 19.5 mL of butanediol diglycidylether (BUDGE) was added. This mixture was shaken at 35° C. for 2 hours. The beads were then washed with 750 mL of Milli-Q® water (Millipore Corp, Billerica, Mass.) and equilibrated with 250 mL of 10 mM NaHCO$_3$.

Immediately following the BUDGE activation step, 10 mL of the filtered bead cake was added to 10 mL solution of 10 mM NaHCO$_3$ containing a 30 g/L concentration of n-Protein A. The beads were rotated in a hybridizer at 37° C. for 2 hours. After two hours, the beads were washed with 30 mLs of Milli-Q® water (Millipore Corporation, Billerica, Mass.). The filter bead cake (10 mL) was added to a jar containing a 10 mL solution comprised of 1 mL of thioglycerol and 9 mL of a buffer solution with 0.2M NaHCO$_3$ and 0.5M NaCl. The mixture was slurried and rotated overnight at room temperature. The beads were then washed with 30 mLs of the following buffers: 0.1M Tris Buffer (pH 8), 0.1M Tris Buffer with 0.15M NaCl (pH 8), 50 mM acetic acid (pH 4.5), PBS (pH 7.4) with 0.002% sodium azide. The beads were then characterized for static capacity as described and Protein A ligand density using the standard BCA assay (Pierce, Rockford, Ill.) using n-Protein A for the standard curve, see Table 1 below.

Example 7

Ligand Assisted Coupling Using Quaternary Amine Ligands, Butanediol Diglycidylether and n-Protein A The beads in Example 7 are identical to beads described in Example 6, with the exception of the associative group addition. The agarose beads were reacted with positively charged associative groups, e.g., cations, according to the following method: 50 mL of beads were added to 25 g of 75% wt GTMAC, 25 mL Milli-Q® water and 1.67 g 50% wt sodium hydroxide. The reaction was shaken vigorously (>100 rpm) on a rotary shaker overnight at room temperature. The beads were then filtered and washed with three 100 mL volumes of Milli-Q® water (Millipore Corporation, Billerica, Mass.). All the subsequent steps (BUDGE activation and Protein A coupling) were identical to those described in Example 6. The beads were then characterized for static capacity as described and Protein A ligand density using the standard BCA assay (Pierce, Rockford, Ill.) using n-Protein A for the standard curve, see Table 1 below.

Example 8

Ligand Assisted Coupling Using Quaternary Amine Ligands, Butanediol Diglycidylether and n-Protein A The beads in example 8 are identical to beads described in example 6, with the exception of the associative group addition. The agarose beads were reacted with positively charged associative groups, e.g., cations, according to the following method: 50 mL of beads were added to 10 g of 75% wt GTMAC, 40 mL Milli-Q® water (Millipore Corporation, Billerica, Mass.) and 1.67 g 50% wt sodium hydroxide. The reaction was shaken vigorously (>100 rpm) on a rotary shaker overnight at room temperature. The beads were then filtered and washed with three 100 mL volumes of Milli-Q® water (Millipore Corporation, Billerica, Mass.). All the subsequent steps (BUDGE activation and Protein A coupling) were identical to those described in Example 6. The beads were then characterized for static capacity as described and Protein A ligand density using the standard BCA assay (Pierce, Rockford, Ill.) using n-Protein A for the standard curve, see Table 1 below.

TABLE 1

Summary of Media Characteristics for Examples 6-8

| | Associative Ligand Density (µmol/mL) | Static Capacity (g/L) | Protein A Ligand Density (g/L) |
|---|---|---|---|
| Example 6 | 20-40 | 71 | 15 |
| Example 7 | 10-20 | 68 | 14 |
| Example 8 | 5-10 | 64 | 12 |
| Q-Sepharose FF | 170-180 | | |
| Mabselect | | 55 | 9 |

Example 9

Ligand Assisted Coupling Using Quaternary Amine Ligands, Epichlorohydrin and n-Protein A on CPG Controlled pore glass (CPG) (Millipore Corporation, Billerica, Mass.) LCA-CPG 1000 A, was used to couple Protein A to CPG using an associative group. LCA-CPG (10 mL) was added to 10 mL aqueous solution containing 50% wt glycidyl trimethylammonium chloride. The reaction was shaken lightly (<100 rpm) overnight at 30° C. The CPG was then washed with 50 mL of Milli-Q® water (Millipore Corporation, Billerica, Mass.) and filter into a dry cake. The CPG was then added to 35 mL of an aqueous solution of epichlorohydrin (6% wt) shaken lightly at 30° C. for 2 hours. The beads were then washed with 100 mL of Milli-Q® water (Millipore Corporation, Billerica, Mass.) and then filtered into a dry cake. The beads (5 mL) were added to 5 mL of 0.01M NaHCO$_3$ containing a 15 mg/mL concentration of n-Protein A. The coupling reaction was lightly shaken overnight at 35° C. The beads were then washed with 100 mL of Milli-Q® water (Millipore Corporation, Billerica, Mass.) and then filtered into a dry cake. The beads were then added to 10 mL of 1M ethanolamine in 0.1 M Tris buffer at pH 8. The reaction was allowed to proceed for 1 hour and then the beads were washed with 50 mL each of 0.2 M NaHCO$_3$, 0.1 M sodium acetate with 0.5 M NaCl (pH 4.5) and then finally with phosphate buffered saline. The static capacity was determined as previously described and the results are shown in Table 2. The associative group concentration was determined by elemental analysis.

Example 10

Ligand Coupling of n-Protein A Without Using Quaternary Amine Ligands, and Epichlorohydrin on CPG Controlled pore glass (CPG) (Millipore Corporation, Billerica, Mass.) ProSep 5-CHO 1000 A, was used to couple Protein A to CPG without using an associative group. The 5-CHO beads (5 mL) were added to 5 mL of 0.01M NaHCO$_3$ containing a 15 mg/mL concentration of n-Protein A. The coupling reaction was lightly shaken overnight at 35° C. The beads were then washed with 100 mL of Milli-Q® water (Millipore Corporation, Billerica, Mass.) and then filtered into a dry cake. The beads were then added to 10 mL of 1M ethanolamine in 0.1 M Tris buffer at pH 8. The reaction was allowed to proceed for 1 hour and then the beads were washed with 50 mL each of 0.2 M NaHCO$_3$, 0.1 M sodium acetate with 0.5 M NaCl (pH 4.5) and then finally with phosphate buffered saline. The static capacity was determined as previously described and the results are shown in Table 2. The associative group concentration was determined by elemental analysis.

TABLE 2

Summary of Media Characteristics for Examples 9 and 10

|  | Associative Ligand Density (µmol/mL) | Static Capacity (g/L) | Protein A Ligand Density (g/L) |
|---|---|---|---|
| Example 9 | 61 | 65 | >10 |
| Example 10 | 0 | 40 | 6 |

Example 11

Determination of Associative Group Concentration: Titration of Quaternary Amine Ligands The quarternary amine ligand density was determined using acid-base titration. A 1 mL sample of beads was placed in a disposable plastic column and then equilibrated with Milli-Q® water (10 mL) (Millipore Corp, Billerica, Mass.) and 1 M NaOH (10 mL). The beads were then washed with 4 mL of Milli-Q® water (Millipore Corp, Billerica, Mass.) and filtered to form a wet bead cake. The beads were added to 80 mL of 1 M NaCl in a small glass beaker with a stir bar. A pH meter was placed in the beaker. The sample was titrated with 0.01 M HCl. A strong anion exchange bead (Q-Sepharose FF) was used as a control. Data for examples 6-8 is shown below in Table 1. The results surprisingly demonstrate that lower associative group density and a correspondingly lower ligand density provides for superior static capacity compared to both commercially available alternatives and alternative experimental conditions.

Example 12

Determining IgG Static and Dynamic Capacity

The static or saturation capacity for each of the products described in the examples above and commercial benchmarks were determined using the following method:
1. Bead suspensions (20% beads) were made out of each sample in PBS buffer.
2. The bead suspensions were stirred and 500 µL samples were pipetted into three 15 mL plastic conical tubes
3. Protein Solution (IgG)(1 mg/ml) in PBS was added to each tube (14 mL).
4. The tubes were capped and shaken slowly (<100 rpm) on an orbital shaker.
5. After 24 hours the beads were allowed to settle and a UV reading was taken of the solution after binding.
6. The UV absorbance was converted into IgG concentration (ε~1.38) and the mass balance was used to determine the saturation capacity.

Figure 1:
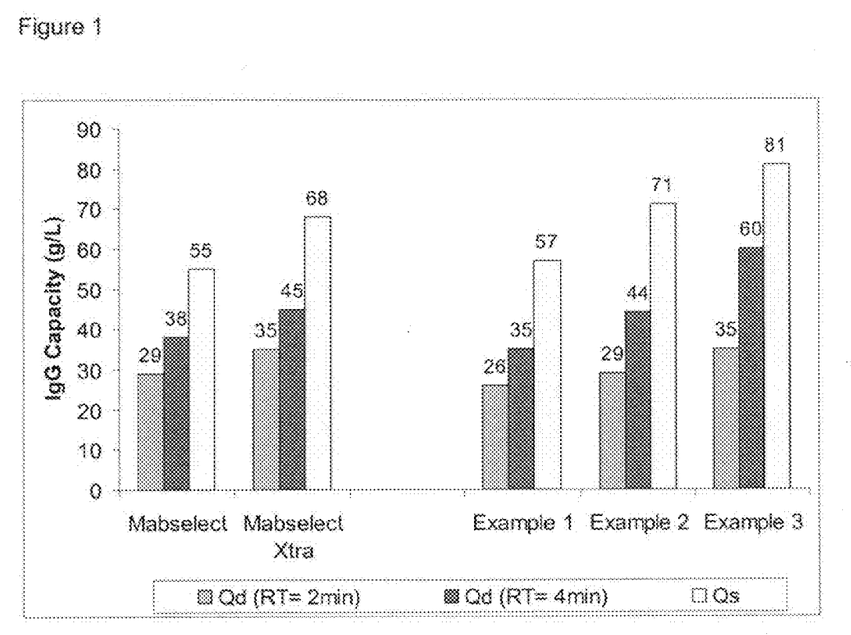
FIG. 1 is a graph showing the dynamic and static capacities of various affinity chromatography media comprising protein A.
Figure 2:
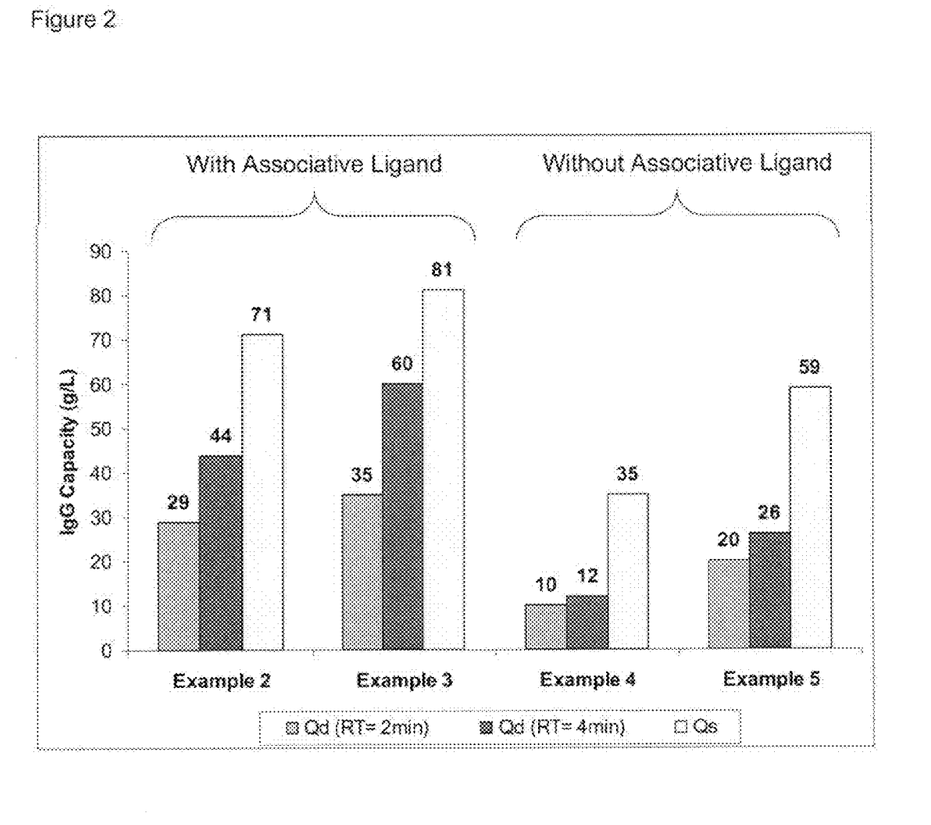
FIG. 2 is a graph comparing the binding capacities of various chromatography media coupled with and without an associative group and ligand assisted Protein A coupling methods according to the invention.

The Protein A media were packed into Omnifit columns (0.66 cm diameter, 7 cm bed height) and tested for dynamic binding capacity of polyclonal human immunoglobulin (IgG). The columns were equilibrated with PBS buffer (pH 7.4) and the protein (1 g/L) was loaded onto the column with this same buffer. The capacity at 10% breakthrough was used to compare the different media. FIG. 1 shows how the static and dynamic capacity for IgG compares for two commercially available benchmarks, Mabselect® and Mabselect Xtra® (GE Healthcare, Piscataway, N.J.) and the product of Examples 1-3. The results for examples 2-5 are shown in FIG. 2. Table shows the static capacity for examples 6-8. Table 2 has the static capacity for examples 9-10.

Example 13

Figure 3:
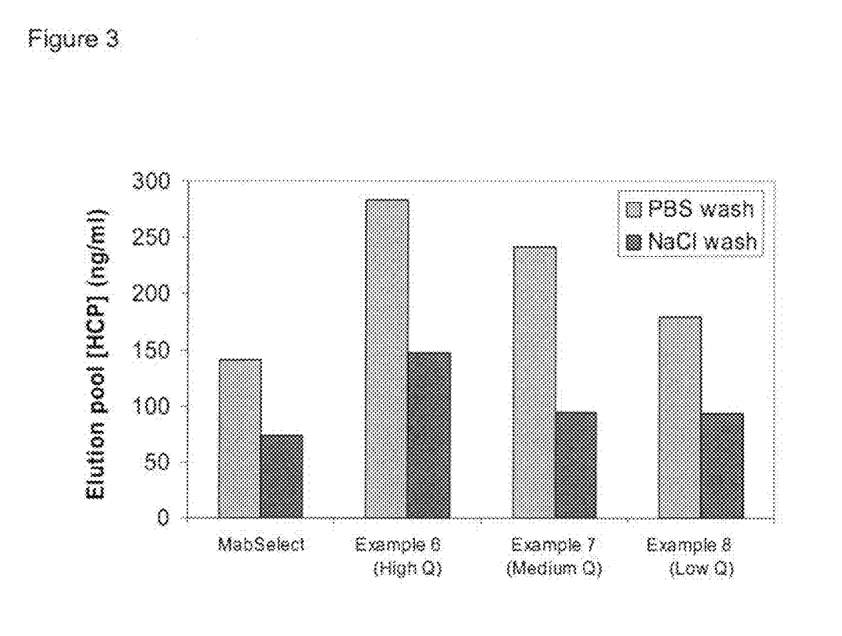
FIG. 3 is a graph showing the measured CHO Cell protein (CHOP) levels in the elution pool and also shows host cell protein binding to media with differing amounts of associative group, with and without an intermediate salt buffer wash. The IgG recoveries were all similar, ~90-95%.

Host Cell Protein (HCP) Level in IgG Elution Pool for Different Associative Ligand Densities with and without an Intermediate Wash A clarified, monoclonal antibody (mAb), serum-free CHO culture (Angel Biotechnology, Northumberland, UK) was used as a model HCP feedstock. After equilibrating with 10 column volume (CV) of phosphate buffered saline (PBS, pH 7.4-7.5, conductivity 15-17 mS/cm) solution, 20 CV of the feed was loaded on a column (0.66 cm inner diameter×7 cm length) packed with the protein A media as described in Examples 6-8. The column was then washed with 10 CV of PBS or 8 CV of PBS (pH 7.4-7.5) supplemented with 1 M NaCl followed with 2 CV of non-supplemented PBS (pH 7.4-7.5) flush. This was followed by 10 CV of 0.1 M sodium citrate (pH 3) elution buffer. The peak fraction was collected from 0.5 to 5.5 CV. The column was then cleaned with 5 CV of 6 M guanidine hydrochloride and then re-equilibrated with PBS buffer. The bind-elute experiments were performed on a BioCad® preparative liquid chromatography system (Applied Biosystems Inc., Foster City, Calif.). The elution pool was measure by UV absorbance at 280 nm to determine IgG concentration and yield. It was also analyzed for CHOP concentration using a commercial enzyme-linked immunosorbent assay (ELISA) kit (Cygnus Technologies Inc., Southport, N.C.). Results are shown in FIG. 3 and demonstrate that non-specific binding associated with higher protein ligand density is easily off-set with the appropriate intermediate wash buffer. When combined with the results shown in Table 1, the data suggest that the flexibility of the method and matrices described herein allow an artisan to maximize desirable capacity while minimizing undesirable side effects such as non-specific binding, thus providing an affinity matrix which may be tailored to a specific application.

Example 14

Reduction of Host Cell Protein (HCP) and DNA Levels in IgG Elution Pool using Intermediate Wash with Salt Buffer A clarified, non-IgG-expressing, serum-free CHO culture (Lampire Biological Laboratories, Piperville, Pa.) was used as a model HCP feedstock and it was spiked with 1 mg/ml of polyclonal human gamma globulin (hIgG) (SeraCare Life Sciences, Inc., Oceanside, Calif.). After equilibrating with 10 column volume (CV) of phosphate buffered saline (PBS, pH 7.4-7.5, conductivity 15-17 mS/cm) solution, 20 CV of the feed was loaded on a column (0.66 cm inner diameter×7 cm length) packed with the protein A media as described in Example 2. The column was then washed with 8 CV of PBS (pH 7.4-7.5) supplemented with 0-1 M NaCl followed with 2 CV of non-supplemented PBS (pH 7.4-7.5) flush. This was followed by 10 CV of 0.1 M sodium citrate (pH 3) elution buffer. The peak fraction was collected from 0.5 to 5.5 CV. The column was then cleaned with 5 CV of 6 M guanidine hydrochloride and then re-equilibrated with PBS buffer. The bind-elute experiments were performed on a BioCad preparative liquid chromatography system (Applied Biosystems Inc., Foster City, Calif.). The elution pool was measure by UV absorbance at 280 nm to determine IgG concentration and yield. It was also analyzed for CHOP concentration using a commercial enzyme-linked immunosorbent assay (ELISA) kit (Cygnus Technologies Inc., Southport, N.C.).

Figure 4A:
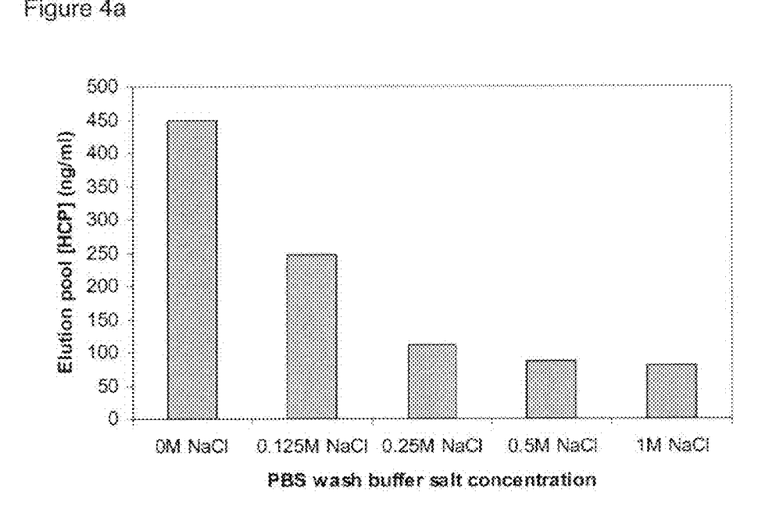
FIG. 4a is a graph showing the reduction of host cell protein levels in the elution pool from a protein A media made via ligand assisted coupling chemistry by performing an intermediate salt wash.

FIG. 4a shows the measured CHOP levels in the elution pool using different salt wash buffers. Increasing NaCl concentration from 0 to 1 M decreased the CHOP concentration by more than five fold, from 450 ng/ml to 80 ng/ml. The IgG recoveries were all similar, ~90-95%.

Figure 4B:
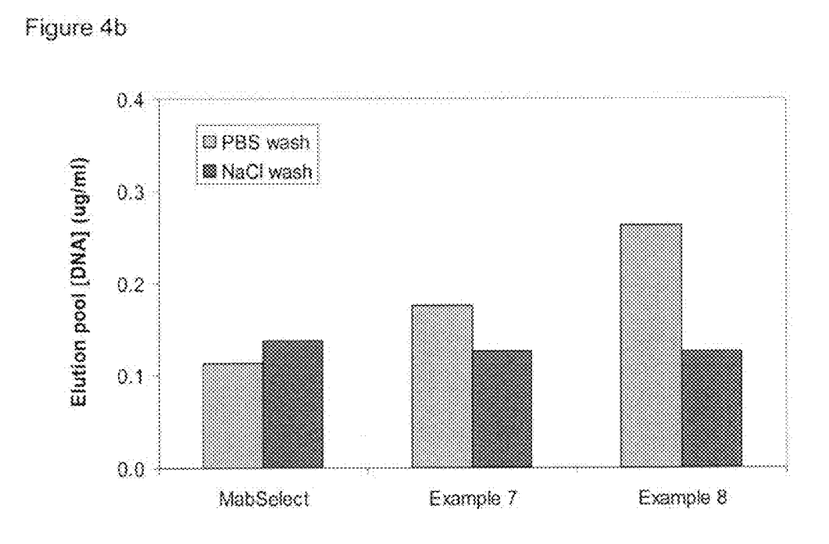
FIG. 4b is a graph showing the reduction of DNA levels in the elution pool from a protein A media made via ligand assisted coupling chemistry by performing an intermediate salt wash.

FIG. 4b shows the measured DNA levels in the elution pool using 1M NaCl-supplemented PBS buffer wash. Salt wash decreased the non-specifically adsorbed DNA levels by 20-60% as compared to regular PBS wash for protein A samples made from ligand assisted coupling.

Example 15

Reduction of HCP Level in IgG Elution Pool using Intermediate Wash with Lower pH and Higher Salt Concentration The experiments were conducted under conditions that were similar to those described above in Example 14, except that an intermediate wash buffer comprising 8 CV of PBS (pH 6.5 and supplemented with 0.4 M NaCl) was used.

Figure 5:
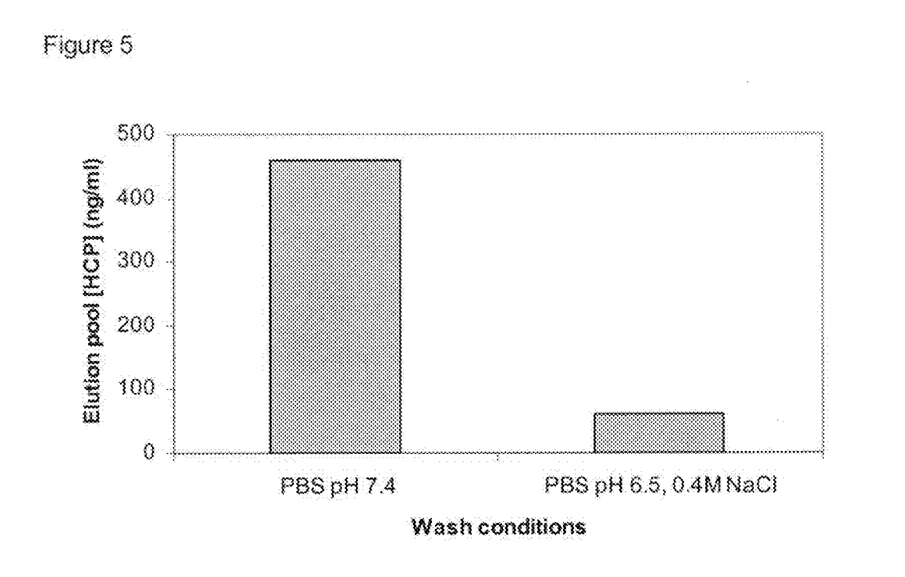
FIG. 5 is a graph showing the reduction of host cell protein levels in the elution pool from a protein A media made via ligand assisted coupling chemistry by performing an intermediate wash using a buffer with different pH and salt concentration.

FIG. 5 shows the measured CHOP levels in the elution pool using intermediate wash buffers with different pH and salt concentrations. Results obtained using the pH 6.5 PBS buffer with 0.4 M NaCl lowered the CHOP level by a factor of ~8, when compared to results obtained using non-supplemented PBS (pH 7.4-7.5) buffer washing step.

Example 16

Reduction of HCP Level in IgG Elution Pool using Intermediate Wash with Buffers Containing Amino Acid or Alkylated Amino Acid The experiments were conducted under conditions that were similar to those described in Example 14, except that an intermediate wash buffer comprising 8 CV PBS buffer (pH 7.4-7.5, conductivity 15-17 mS/cm) and 0.25-0.5 M betaine, L-alanine glycine, or lysine, or 0.125-0.25 M valine, or 0.15 M glutamic acid was used.

Figure 6A:
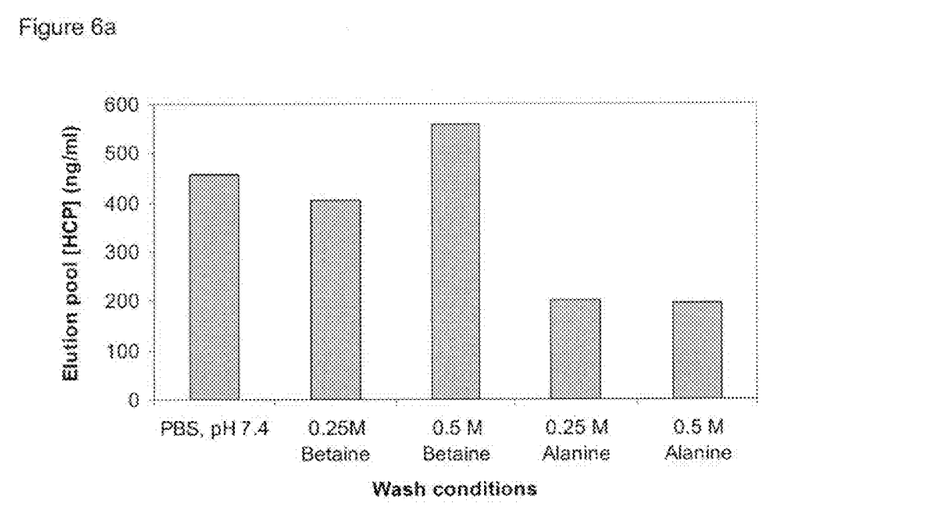
FIG. 6a is a graph showing the reduction of host cell protein levels in the elution pool from a protein A media made via ligand assisted coupling chemistry by performing an intermediate wash using a buffer containing alanine or betaine.

FIG. 6a shows the measured CHOP levels in the elution pool using intermediate wash buffers containing betaine and L-alanine. 0.25 M betaine reduced the CHOP concentration. Comparatively, alanine was more effective than betaine. At both concentrations of alanine, the bound CHOP was reduced by more than 2-fold.

Figure 6B:
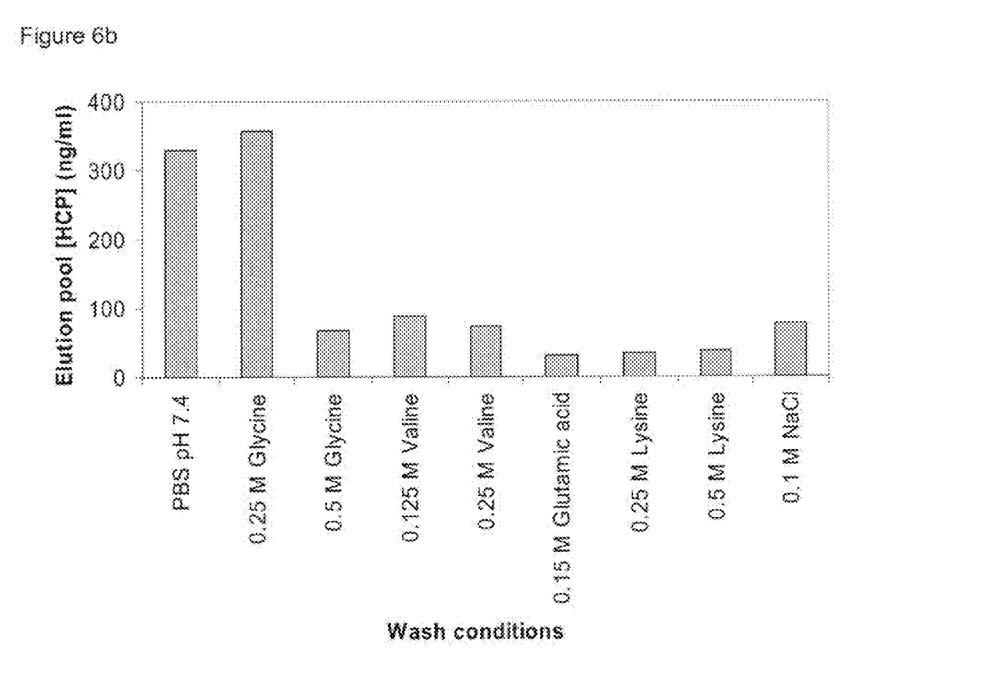
FIG. 6b is a graph showing the reduction of host cell protein levels in the elution pool from a protein A media made via ligand assisted coupling chemistry by performing an intermediate wash using a buffer containing various amino acids.

FIG. 6b shows the measured CHOP levels in the elution pool using intermediate wash buffers containing various concentrations of valine, glycine, glutamic acid, or lysine. Compared to PBS wash, the CHOP levels in the elution pool were about 3-10 fold lower with the amino acid washes, among which the lysine and glutamic acid seem to be the most effective.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method or purifying a target molecule from a mixture comprising:
   (1) contacting the mixture comprising the target molecule with an affinity chromatography matrix under a set of pH and/or salt conditions, wherein the affinity chromatography matrix comprises: a) a solid support; b) a protein ligand bound to the solid support, wherein the protein ligand binds to the target molecule under the set of pH and/or salt conditions; c) an activating group bound to the solid support which interacts covalently with the protein ligand: and d) an associative group bound to the solid support, where the associative group interacts non-covalently with the protein ligand and wherein the activating group and the associative group are both linked separately to the solid support: and
   (2) altering the set of pH and/or salt conditions of (1) such that the target molecule no longer binds to the protein ligand of the matrix, thereby purifying the substance of interest.

2. The method of claim 1, wherein the target molecule is an immunoglobulin.

3. The method of claim 1, wherein the target molecule is a fusion protein.

4. The method of claim 3, wherein the fusion protein is an Fc fusion protein.

5. The method of claim 2, wherein the immunoglobulin is a monoclonal antibody.

6. The method of claim 1, further comprising an intermediate washing step to remove contaminants comprising, contacting the solid support with a wash buffer after step (1) and before step (2).

7. The method of claim 6, wherein the contaminants comprise a small molecule, a protein, a nucleic acid or any combination thereof.

8. The method of claim 6, wherein the wash buffer comprises an acidic pH and a salt or both.

9. The method of claim 8, wherein the pH ranges from 5-6.99.

10. The method of claim 6, wherein the wash buffer has a pH ranging from 5.0-8.0.

11. The method of claim 6, wherein the wash buffer has a basic pH and comprises more than 0.0001M NaCl, but less than 0.8M NaCl.

12. The method of claim 11, wherein the pH is 7.4.

13. The method of claim 6, wherein the wash buffer comprises an amino acid or an alkylated amino acid.

14. The method of claim 13, wherein the amino acid or alkylated amino acid is selected from the group consisting of from L-alanine, betaine, glycine valine, glutamic acid, and lysine.

15. The method of claim 14, wherein the amino acid is a charged amino acid.

16. The method of claim 1, wherein the solid support is an agarose bead.

17. The agarose bead of claim 16, wherein the bead comprises at least 10g/L of protein A bound to the surface of the agarose bead.

\* \* \* \* \*